US009694338B2

(12) United States Patent
Murphy et al.

(10) Patent No.: US 9,694,338 B2
(45) Date of Patent: Jul. 4, 2017

(54) COVALENTLY-IMMOBILIZED HYDROGEL ARRAYS IN MULTI-WELL PLATES

(71) Applicant: Wisconsin Alumni Research Foundation, Madison, WI (US)

(72) Inventors: William Murphy, Waunakee, WI (US); Ngoc Nhi Le, Norcross, GA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/575,084

(22) Filed: Dec. 18, 2014

(65) Prior Publication Data
US 2016/0175800 A1    Jun. 23, 2016

(51) Int. Cl.
*B01J 19/00* (2006.01)
*G01N 33/50* (2006.01)

(52) U.S. Cl.
CPC ...... *B01J 19/0046* (2013.01); *G01N 33/5026* (2013.01); *G01N 33/5032* (2013.01); *G01N 33/5064* (2013.01); *G01N 33/5073* (2013.01); *B01J 2219/0059* (2013.01); *B01J 2219/00315* (2013.01); *B01J 2219/00626* (2013.01); *B01J 2219/00637* (2013.01); *B01J 2219/00644* (2013.01); *B01J 2219/00659* (2013.01); *B01J 2219/00675* (2013.01); *B01J 2219/00711* (2013.01); *B01J 2219/00725* (2013.01); *B01J 2219/00736* (2013.01); *B01J 2219/00756* (2013.01)

(58) Field of Classification Search
None
See application file for complete search history.

(56) References Cited

U.S. PATENT DOCUMENTS

| 2004/0029241 A1* | 2/2004 | Hahn et al. ......... | A61K 9/1641 435/174 |
| 2005/0244983 A1* | 11/2005 | Ching .................. | G01N 33/52 436/172 |

OTHER PUBLICATIONS

Cordey et al., "Enhancing the Reliability and Throughput of Neurosphere Culture on Hydrogel Microwell Arrays," Stem Cells 2008, 26:2586-2594.*
Lin et al., "PEG hydrogels formed by thiol-ene photo-click chemistry and their effect on the formation and recovery of insulin-secreting cell spheroids," Biomaterials 2011, 32:9685-9695.*
Polizzotti et al., Three-Dimensional Biochemical Patterning of Click-Based Composite Hydrogels via Thiolene Photopolymerization; Biomacromolecules 2008, 9:1084-1087.
Fairbanks et al., A versatile Synthetic Extracellular Matrix Mimic via Thiol-Norbornene Photopolymerization, (Adv. Mater 2009, 21:5005-5010).

(Continued)

*Primary Examiner* — Kaijiang Zhang
(74) *Attorney, Agent, or Firm* — Stinson Leonard Street LLP

(57) ABSTRACT

Hydrogel arrays, methods for preparing hydrogel arrays and methods for screening cell-substrate interactions using the hydrogel arrays are disclosed. Advantageously, the hydrogel arrays include individual hydrogel posts that are completely isolatable, allowing for systematic and independent control of the chemical composition and physical dimensions of each hydrogel post.

10 Claims, 4 Drawing Sheets
(4 of 4 Drawing Sheet(s) Filed in Color)

(56) References Cited

OTHER PUBLICATIONS

Nagase et al., Human Matrix Metalloproteinase Specificity Studies Using Collagen Sequence-Based Synthetic Peptides, (Biopolymers 1996, 40:399-416).

Toepke et al., Characterization of Thiol-Ene Crosslinked PEG Hydrogels, Macromolecular Materials and Engineering 2013, 298: 699-703.

Impellitteri et al., Specific VEGF sequestering and release using peptide-functionalized hydrogel microspheres, Biomaterials 2012, 33:3475-84.

Belair et al., Specific VEGF sequestering to biomaterials: Influence of serum stability, Acta Biomater. 2013.

Gould et al., Small peptide functionalized thiol—ene hydrogels as culture substrates for understanding valvular interstitial cell activation and de novo tissue deposition, Acta Biomater 2012, 8:3201-3209.

Seo et al., Attachment of hydrogel microstructures and proteins to glass via thiol-terminated silanes, Colloids Surf B Biointerfaces 2012, 98:1-6.

Halliwell et al., A Factorial Analysis of Silanization Conditions for the Immobilization of Oligonucleotides on Glass Surfaces, Anal Chem 2001, 73:2476-2483.

Cras et al., Comparison of chemical cleaning methods of glass in preparation for silanization, Biosens Bioelectron 1999, 14:683-688.

Vistas et al., Silanization of glass chips—A factorial approach for optimization, Comparison of chemical cleaning methods of glass in preparation for silanization, Appl Surf Sci 2013, 286:314-318.

Nguyen et al., Differential effects of cell adhesion, modulus and VEGFR-2 inhibition on capillary network formation in synthetic hydrogel arrays, Biomaterials 2014, 35:2149-2161.

Hansen et al., Biomaterial arrays with defined adhesion ligand densities and matrix stiffness identify distinct phenotypes for tumorigenic and non-tumorigenic human mesenchymal cell types Biomaterials Science 2014, 5:745-756.

Musah et al., Substratum-induced differentiation of human pluripotent stem cells reveals the coactivator YAP is a potent regulator of neuronal specification, PNAS 2014, 111:13805-13810.

\* cited by examiner

Negative insert surface topography

Hydrogel surface topography

FIG. 3A
FIG. 3B
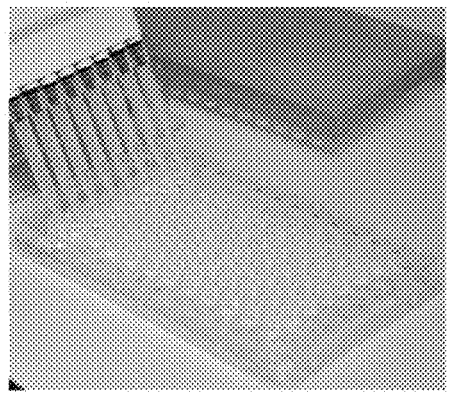
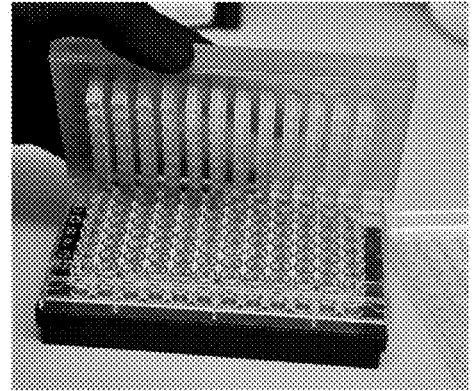
FIG. 3C
FIG. 3D

FIG. 4A
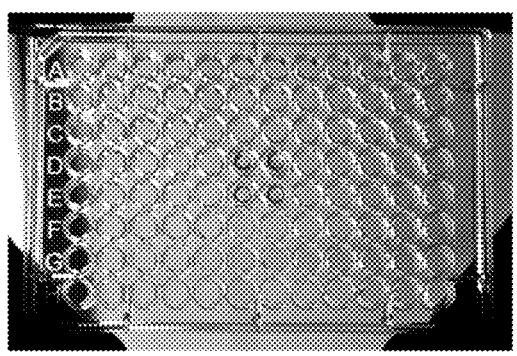
FIG. 4C
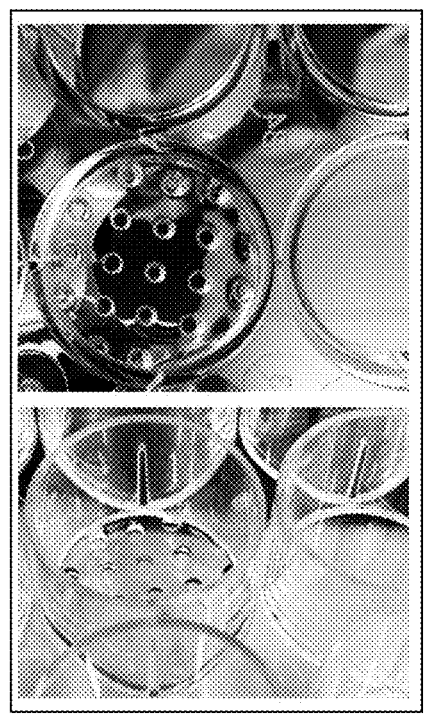
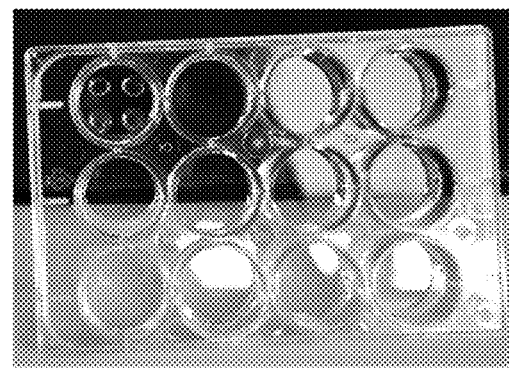
FIG. 4B

```
                        SEQUENCE LISTING

<160> NUMBER OF SEQ ID NOS: 36

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Arg Gly Asp Ser
1

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Cys Arg Gly Asp Ser
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Gly Arg Gly Asp Ser Pro
1               5

<210> SEQ ID NO 4
<211> LENGTH: 22
<212> TYPE: PRT
<213> ORGANISM: Artificial Sequence
<220> FEATURE:
<223> OTHER INFORMATION: Synthetic

<400> SEQUENCE: 4

Cys Arg Gly Asp Gly Gly Gly Gly Gly Gly Gly Gly Gly Gly
1               5                   10                  15

Gly Pro His Ser Arg Asn
            20

<210> SEQ ID NO 5
<211> LENGTH: 19
<212> TYPE: PRT
<213> ORGANISM: Artificial Sequence
<220> FEATURE:
<223> OTHER INFORMATION: Synthetic

<400> SEQUENCE: 5

Cys Arg Gly Asp Ser Gly Ser Gly Ser Gly Ser Gly Ser Gly Pro His
1               5                   10                  15

Ser Arg Asn

<210> SEQ ID NO 6
```

```
<211> LENGTH: 6
<212> TYPE: PRT
<213> ORGANISM: Artificial Sequence
<220> FEATURE:
<223> OTHER INFORMATION: Synthetic

<400> SEQUENCE: 6

Cys Arg Gly Asp Ser Pro
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic

<400> SEQUENCE: 7

Gly Cys Tyr Gly Arg Gly Asp Ser Pro Gly
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Synthetic

<400> SEQUENCE: 8

Arg Gly Asp Phe Cys
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic

<400> SEQUENCE: 9

Arg Asp Gly Ser
1

<210> SEQ ID NO 10
<211> LENGTH: 5
<212> TYPE: PRT
<213> ORGANISM: Artificial Sequence
<220> FEATURE:
<223> OTHER INFORMATION: Synthetic

<400> SEQUENCE: 10

Cys Arg Asp Gly Ser
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic

<400> SEQUENCE: 11

Gly Cys Tyr Gly Arg Gly Asp Ser Pro Gly
1               5                   10

<210> SEQ ID NO 12
<211> LENGTH: 5
```

```
<212> TYPE: PRT
<213> ORGANISM: Artificial Sequence
<220> FEATURE:
<223> OTHER INFORMATION: Synthetic

<400> SEQUENCE: 12

Pro His Ser Arg Asn
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Gly Trp Gly Gly Arg Gly Asp Ser Pro
1               5

<210> SEQ ID NO 14
<211> LENGTH: 13
<212> TYPE: PRT
<213> ORGANISM: Artificial Sequence
<220> FEATURE:
<223> OTHER INFORMATION: Synthetic

<400> SEQUENCE: 14

Ser Ile Asp Gln Val Glu Pro Tyr Ser Ser Thr Ala Gln
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic

<400> SEQUENCE: 15

Gly Arg Asn Ile Ala Glu Ile Ile Lys Asp Ile
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Asp Ile Thr Tyr Val Arg Leu Lys Phe
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic

<400> SEQUENCE: 17

Asp Ile Thr Val Thr Leu Asn Arg Leu
1               5

<210> SEQ ID NO 18
<211> LENGTH: 8
<212> TYPE: PRT
```

<213> ORGANISM: Artificial Sequence
<220> FEATURE:
<223> OTHER INFORMATION: Synthetic

<400> SEQUENCE: 18

Gly Arg Tyr Val Val Leu Pro Arg
1               5

<210> SEQ ID NO 19
<211> LENGTH: 13
<212> TYPE: PRT
<213> ORGANISM: Artificial Sequence
<220> FEATURE:
<223> OTHER INFORMATION: Synthetic

<400> SEQUENCE: 19

Gly Asn Arg Trp His Ser Ile Tyr Ile Thr Arg Phe Gly
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic

<400> SEQUENCE: 20

Gly Ala Ser Ile Lys Val Ala Val Ser Ala Asp Arg
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Gly Thr Thr Val Lys Tyr Ile Phe Arg
1               5

<210> SEQ ID NO 22
<211> LENGTH: 10
<212> TYPE: PRT
<213> ORGANISM: Artificial Sequence
<220> FEATURE:
<223> OTHER INFORMATION: Synthetic

<400> SEQUENCE: 22

Gly Ser Ile Lys Ile Arg Gly Thr Tyr Ser
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic

<400> SEQUENCE: 23

Gly Ser Ile Asn Asn Asn Arg
1               5

<210> SEQ ID NO 24
<211> LENGTH: 9
<212> TYPE: PRT
<213> ORGANISM: Artificial Sequence

```
<220> FEATURE:
<223> OTHER INFORMATION: Synthetic

<400> SEQUENCE: 24

Ser Asp Pro Gly Tyr Ile Gly Ser Arg
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic

<400> SEQUENCE: 25

Tyr Ile Gly Ser Arg
1               5

<210> SEQ ID NO 26
<211> LENGTH: 14
<212> TYPE: PRT
<213> ORGANISM: Artificial Sequence
<220> FEATURE:
<223> OTHER INFORMATION: Synthetic

<400> SEQUENCE: 26

Gly Thr Pro Gly Pro Gln Gly Ile Ala Gly Gln Gly Val Val
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic

<400> SEQUENCE: 27

Gly Thr Pro Gly Pro Gln Gly Ile Ala Gly Gln Arg Val Val
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Synthetic

<400> SEQUENCE: 28

Met Asn Tyr Tyr Ser Asn Ser
1               5

<210> SEQ ID NO 29
<211> LENGTH: 12
<212> TYPE: PRT
<213> ORGANISM: Artificial Sequence
<220> FEATURE:
<223> OTHER INFORMATION: Synthetic

<400> SEQUENCE: 29

Lys Lys Gln Arg Phe Arg His Arg Asn Arg Lys Gly
1               5                   10

<210> SEQ ID NO 30
<211> LENGTH: 18
<212> TYPE: PRT
<213> ORGANISM: Artificial Sequence
<220> FEATURE:
```

<223> OTHER INFORMATION: Synthetic

<400> SEQUENCE: 30

Gly Gly Gly Lys Leu Thr Trp Gln Glu Leu Tyr Gln Leu Lys Tyr Lys
1               5                   10                  15

Gly Ile

<210> SEQ ID NO 31
<211> LENGTH: 15
<212> TYPE: PRT
<213> ORGANISM: Artificial Sequence
<220> FEATURE:
<223> OTHER INFORMATION: Synthetic

<400> SEQUENCE: 31

Lys Leu Thr Trp Gln Glu Leu Tyr Gln Leu Lys Tyr Lys Gly Ile
1               5                   10                  15

<210> SEQ ID NO 32
<211> LENGTH: 12
<212> TYPE: PRT
<213> ORGANISM: Artificial Sequence
<220> FEATURE:
<223> OTHER INFORMATION: Synthetic

<400> SEQUENCE: 32

Lys Ile Pro Lys Ala Ser Ser Val Pro Thr Glu Leu
1               5                   10

<210> SEQ ID NO 33
<211> LENGTH: 20
<212> TYPE: PRT
<213> ORGANISM: Artificial Sequence
<220> FEATURE:
<223> OTHER INFORMATION: Artificial

<400> SEQUENCE: 33

Lys Ile Pro Lys Ala Ser Ser Val Pro Thr Glu Leu Ser Ala Ile Ser
1               5                   10                  15

Thr Leu Tyr Leu
            20

<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Lys Arg Thr Gly Gln Tyr Lys Leu
1               5

<210> SEQ ID NO 35
<211> LENGTH: 14
<212> TYPE: PRT
<213> ORGANISM: Artificial Sequence
<220> FEATURE:
<223> OTHER INFORMATION: Synthetic

<400> SEQUENCE: 35

Lys Cys Gly Gly Pro Gln Gly Ile Trp Gly Gln Gly Cys Lys
1               5                   10

<210> SEQ ID NO 36

```
<211> LENGTH: 14
<212> TYPE: PRT
<213> ORGANISM: Artificial Sequence
<220> FEATURE:
<223> OTHER INFORMATION: Synthetic

<400> SEQUENCE: 36

Lys Cys Gly Gly Pro Gln Gly Ile Ala Gly Gln Gly Cys Lys
1               5                   10
```

COVALENTLY-IMMOBILIZED HYDROGEL ARRAYS IN MULTI-WELL PLATES

STATEMENT REGARDING FEDERALLY SPONSORED RESEARCH OR DEVELOPMENT

This invention was made with government support under HL093282 awarded by the National Institutes of Health. The government has certain rights in the invention.

STATEMENT IN SUPPORT FOR FILING A SEQUENCE LISTING

A paper copy of the Sequence Listing and a computer readable form of the Sequence Listing containing the file named "P140305US01_28243-188_ST25.txt", which is 7318 bytes in size (as measured in MICROSOFT WINDOWS® EXPLORER), are provided herein and are herein incorporated by reference. This Sequence Listing consists of SEQ ID NOs:1-36.

BACKGROUND OF THE DISCLOSURE

The present disclosure relates generally to methods for preparing biomaterial arrays and methods for using the biomaterial arrays. More particularly, the present disclosure relates to hydrogel arrays, methods for preparing hydrogel arrays and methods for screening cell-substrate interactions using the hydrogel arrays. The hydrogel arrays include individual hydrogel posts that are completely isolatable, allowing for systematic and independent control of the chemical composition and physical dimensions of each hydrogel post.

The development of most tissue types involves a complex interplay of multiple signals leading to controlled precursor cell differentiation into mature, tissue-specific cell types. For example, mesenchymal stem cells (MSCs) may be differentiated in vitro into osteoblasts, chondrocytes, myoblasts, adipocytes, neurons, and endothelial cells by exposure to a variety of growth factors. Exposure to growth factors may be controlled by the media and the substrates upon which the cells are cultured. Substantial progress has been made in the development of defined media, but only more recently has the role of substrates and cell-substrate adhesion on cell growth been examined.

Based on studies to determine defined media, it has become apparent that the substrate is important for successful cellular growth and tissue generation. For example, it has been demonstrated that attachment to the substrate by human embryonic stem cells may contribute to the variability in whether the cells remain undifferentiated or undergo differentiation. Therefore, it is important to not only identify cell culture media for successful cell culture conditions, but to also identify defined substrates.

Screening well-defined surfaces in an array format allows rapid identification of specific molecules that promote cellular adhesion, cellular spreading, proliferation, migration and differentiation, as well as molecules that regulate cell behavior. Biomaterial arrays such as self-assembled monolayers ("SAMs") in array formats (i.e., SAM arrays) have been constructed that present ligands to cells plated onto the array. A SAM is an organized layer of amphiphilic molecules in which one end of the molecule exhibits a specific, reversible affinity for a substrate and the other end of the molecule has a functional group. The use of alkanethiols to construct SAM arrays allow for the formation of reproducible SAM arrays and surfaces. SAM arrays may be used to identify specific ligands or epitopes that promote cellular attachment, spreading, proliferation, migration and differentiation. Additionally, SAM arrays may be patterned such that ligands will be presented to the cells in defined areas of the array.

Biomaterial array patterning approaches have been developed to spatially localize ligands to create spatially and chemically-defined cell culture substrates. Microcontact printing, for example, generates patterned SAM arrays by "inking" alkanethiolate molecules onto a flexible elastomeric stamp and stamping the alkanethiolates onto a gold surface, which transfers a pattern of ligands onto the gold substrate. The remaining areas of bare gold are then "backfilled" with a second alkanethiolate species to generate a bio-inert SAM surrounding the stamped hydrophobic alkanethiolate domains. The substrates are then bathed in a solution of ligands that spontaneously adsorb to the hydrophobic alkanethiolate regions to create patterned islands for cell attachment. Microfluidics approaches for SAM array patterning typically use elastomeric stamps with microscale features that form channels when passively adhered to a SAM. Localized ligand conjugation can then be achieved by flowing reaction solutions through the channels exposing them to reactive terminal moieties presented by the underlying SAM. Photochemistry in combination with micro-patterned photomasks can be used to create patterned SAM arrays by selectively protecting a reactive terminal moiety and then selectively deprotecting the terminal moiety to locally immobilize ligands on the SAM. SAM array patterning can also be accomplished by locally destroying/removing regions of a fully formed SAM, then reforming new SAMs in the destroyed regions.

While biomaterial arrays such as SAM arrays provide an excellent model substrate for investigating the effects of an immobilized ligand on cell behavior, preparing SAM array platforms using less labor intensive processes are needed to make SAM array use more widespread. Accordingly, there exists a need for alternative methods for preparing biomaterial arrays to identify surfaces that will support survival and growth of cells in culture, allow rapid identification of specific molecules that promote cellular adhesion, cellular spreading, proliferation, migration, differentiation and regulate cellular behavior.

BRIEF DESCRIPTION OF THE DISCLOSURE

The present disclosure relates generally to methods for preparing biomaterial arrays and methods for using the biomaterial arrays. More particularly, the present disclosure relates to hydrogel arrays, methods for preparing hydrogel arrays and methods for screening molecule-molecule interactions using the hydrogel arrays.

In accordance with the present disclosure, methods for preparing hydrogel arrays to identify surfaces that will support survival and growth of cells in culture, allow rapid identification of specific molecules that promote cellular adhesion, cellular spreading, proliferation, migration, differentiation and regulate cellular behavior have been discovered. The hydrogel arrays of the present disclosure can also be used for two-dimensional (2D) and three-dimensional (3D) cell culture. The hydrogel arrays of the present disclosure can further be used for two-dimensional enrichment of biomolecules such as, for example, biomolecules, to cell surfaces using soluble factor binding peptides. The hydrogel arrays of the present disclosure can also be used as sources for soluble factors by encapsulating cells and soluble-factor releasing microparticles, which can be used to promote angiogenesis, promote tubulogenesis, promote morphogenic processes and screening for drug toxicity, for example. Additionally, the hydrogel arrays of the present disclosure can be used to analyze molecule-molecule interactions such as, for example, ligand-target interactions, antibody-antigen interactions, protein-protein interactions, growth factor-binding ligand interactions, receptor-ligand interactions and the like. Use of the hydrogel arrays of the present disclosure to analyze molecule-molecule interactions can allow for determining specificity of binding, affinity of binding and the like.

In one aspect, the present disclosure is directed to methods for preparing a hydrogel array. The methods generally allow for polymerization pattering of hydrogels covalently immobilized to the center of wells within a multi-well plate. The methods offer the ability to form hydrogel arrays whereby each hydrogel post in the array is completely isolatable. The hydrogel array formation process allows for systematic and independent control of the chemical composition and physical XYZ-dimensions of each hydrogel post of the array. The output allows for systematic and independent control of the soluble factors presented to each hydrogel post in the array.

Particularly, in one embodiment, the present disclosure is directed to a method of preparing a hydrogel array comprising a multi-well plate, the multi-well plate comprising a plurality of wells wherein the plurality of wells independently comprises at least one hydrogel post. The method includes: thiol-functionalizing a bottom surface of the plurality of wells; adding a hydrogel precursor solution to at least one well of the plurality of wells; selectively polymerizing a portion of the hydrogel precursor solution in the at least one well; and removing unpolymerized hydrogel precursor solution from the plurality of wells, wherein the polymerized hydrogel forms at least one hydrogel post covalently immobilized within the at least one well. In one embodiment, the thiol-functionalizing of the bottom surface of the plurality of wells is by silanization.

In another aspect, the present disclosure is directed to a hydrogel array including a multi-well plate that comprises a plurality of wells and at least one hydrogel post covalently-immobilized to a surface of a well of the plurality of wells. The at least one hydrogel post fills a portion of the surface of the well. In one embodiment, the hydrogel array is prepared using the methods generally described herein.

In yet another aspect, the present disclosure is directed to a method for screening molecule-molecule interactions. The method includes preparing a hydrogel array comprising at least one hydrogel post in a well of the hydrogel array. The at least one hydrogel post is prepared by a method including: thiol-functionalizing a bottom surface of a well of a multi-well plate; adding a hydrogel precursor solution comprising at least one ligand to the well; assembling the multi-well plate with a photomask; selectively polymerizing the hydrogel precursor solution in the well; removing unpolymerized hydrogel precursor solution from the well, wherein the polymerized hydrogel forms at least one hydrogel post covalently-immobilized to the well, wherein the multi-well plate comprising the hydrogel post in the well forms the hydrogel array; contacting the hydrogel post with a molecule known to or suspected of interacting with the at least one ligand; and analyzing the hydrogel array. In one embodiment, the thiol-functionalizing of the bottom surface of a well is by silanization.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein:

FIGS. 3A-3D depict an exemplary method of preparing a hydrogel array in wells of a glass bottom 96-well plate.

FIGS. 4A-4C depict exemplary hydrogel arrays as prepared using the methods of the present disclosure: (A) depicts a 96-well hydrogel array with one hydrogel post in each of the wells; (B) depicts a 12-well hydrogel array with one hydrogel post in each of the wells; and (C) depicts a 12-well hydrogel array with a hydrogel post containing a well.

Figure 1:
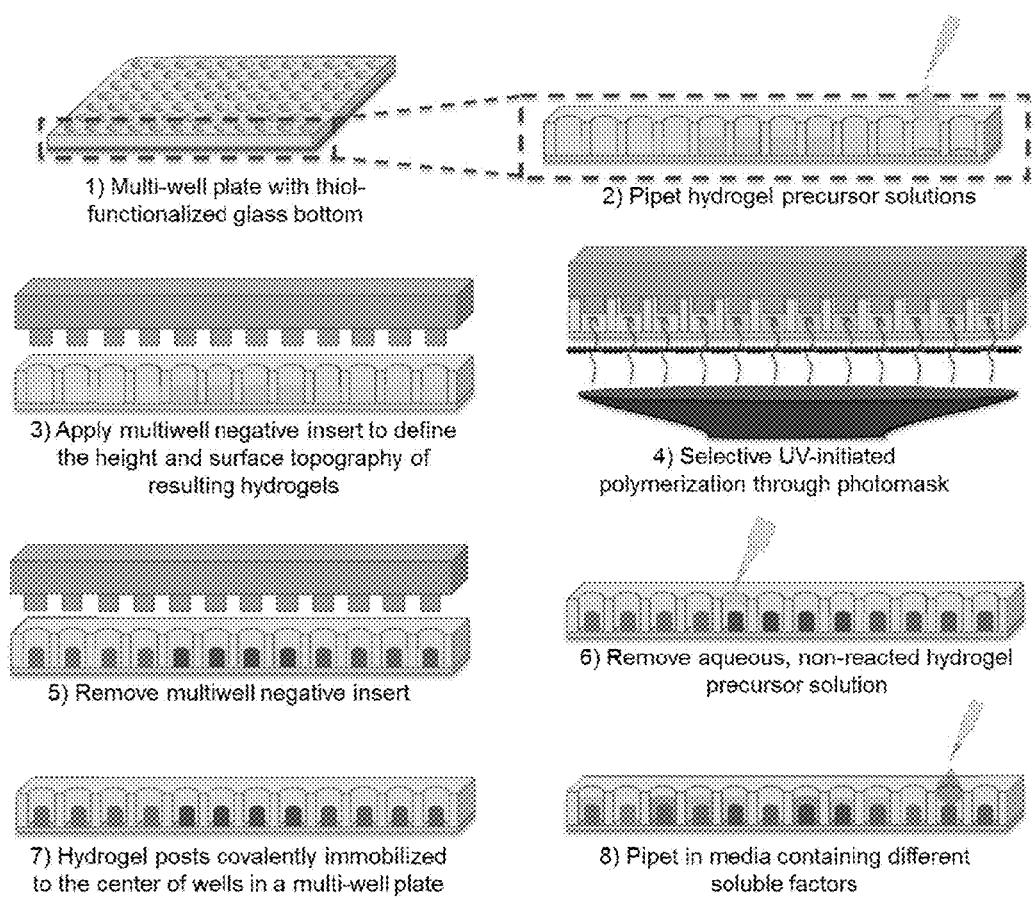
FIG. 1 is a schematic illustration of the steps for preparing a hydrogel array of the present disclosure.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF THE DISCLOSURE

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In accordance with the present disclosure, methods for preparing biomaterial arrays for screening molecule-molecule interactions have been discovered. More particularly, the present disclosure relates to hydrogel arrays. In one aspect, hydrogel arrays can be prepared with controlled hydrogel modulus, hydrogel polymer density, hydrogel crosslinker density, hydrogel ligand identity and hydrogel ligand density and to methods for preparing the hydrogel arrays. It has been found that the hydrogel arrays with controlled hydrogel modulus, hydrogel polymer density, hydrogel crosslinker density, hydrogel ligand identity and hydrogel ligand density offer an improved screening method for molecule-molecule interactions. Further, the hydrogel arrays of the present disclosure are prepared to include completely isolatable hydrogel posts.

The hydrogel arrays of the present disclosure can be functionalized with biomolecules and are compatible with cell culture. The hydrogel arrays of the present disclosure can also be used to alter (e.g., enhance, inhibit and change) cell function such as, for example, cell proliferation, cell differentiation, cell self-renewal, cell spreading, cell attachment, cell-cell contact, cell contractility, cell migration, tissue formation and self-organization of cells to form cell-cell contacts and organization leading to tissue formation.

As known by those skilled in the art, a hydrogel is a network of polymer chains that are hydrophilic in which a polymeric material and water are in an equilibrated form.

The hydrogel is formed using unpolymerized starting components. The polymeric material can be, for example, a natural polymer material, a synthetic polymer material and combinations thereof.

The methods for preparing hydrogel arrays of the present disclosure advantageously allow for systematic and independent control of the chemical composition and physical XYZ dimensions of each hydrogel post without the need for post-processing modifications such as through chemical or physical barriers to prevent diffusion between hydrogel posts. In this way, independent control of the soluble factors presented to each hydrogel post in the array is provided without the increased handling steps and complexity previously required.

Methods for Preparing Patterned Hydrogel Arrays

In one aspect, the present disclosure is directed to a method for preparing a hydrogel array. The method generally includes thiol-functionalizing a bottom surface of a plurality of wells in a multi-well plate; adding a hydrogel precursor solution to at least one well of the plurality of wells; selectively polymerizing a portion of the hydrogel precursor solution in the at least one well; and removing unpolymerized hydrogel precursor solution from the plurality of wells. The polymerized hydrogel forms at least one hydrogel post covalently immobilized within the at least one well. As used herein, "hydrogel post" refers to the hydrogel material remaining, and covalently immobilized to, at least a portion of the surface of a well of the multi-well plate. That is, the "hydrogel post" is surrounded by a background that is substantially free, and even completely free, of hydrogel ("hydrogel-free").

The multi-well plates for use in the methods of the present disclosure includes any multi-well plate known in the art, including for example, 4-well plates, 6-well plates, 8-well plates, 12-well plates, 24-well plates, 32-well plates, 96-well plates, and 384-well plates. The multi-well plates can be a glass-bottom multi-well plate or a polystyrene multi-well plate as commonly used in the art.

It should be understood that the size of the individual wells of the multi-well plates will at least partially determine the size of the resulting hydrogel posts and hydrogel arrays. Specifically, the diameter and depth of the wells will constrain the diameter and the height of the resulting hydrogel posts, and therefore, will constrain the thickness and size of the resulting hydrogel array.

It should be understood that while silanizing can be used to allow the bottom surface of the plurality of wells in the multi-well plate to hold the hydrogel posts to the surface of the well, it should be understood by one skilled in the art that silanizing is not necessarily required, particularly when the multi-well plate is a polystyrene multi-well plate.

Figure 2A:
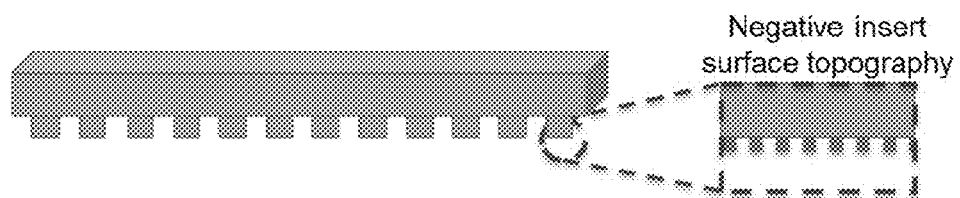
FIGS. 2A & 2B depict an exemplary multi-well plate and negative insert for use in the methods of the present disclosure.
Figure 2B:
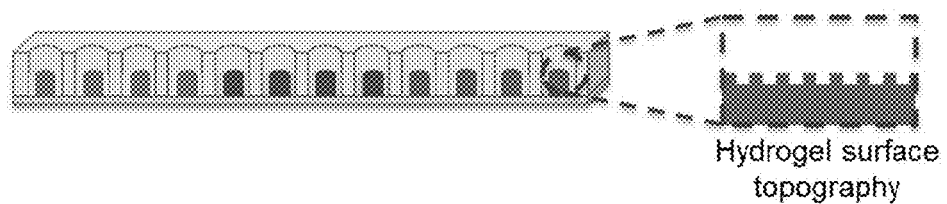

In some embodiments, the multi-well plate is assembled with a negative insert (see FIGS. 2A & 2B). The negative insert fills a portion within at least one well of the multi-well plate and functions to define the height (or thickness) and/or topography of the hydrogel post within the well of the formed hydrogel array. A negative insert may be particularly desirable when preparing shorter hydrogel posts (i.e., thinner hydrogel arrays). Thus, the hydrogel posts can have any desirable height, and further, the heights of the posts can vary from one hydrogel post to another by altering the dimensions of the negative insert. Suitable heights of the hydrogel posts can be from about 20 micrometers (μm) to about 1 millimeter, however, hydrogel posts can be made much higher than 1 millimeter if desired.

The height of the hydrogel posts, and thus the thickness of the resulting hydrogel posts are significant as when formed, the hydrogel naturally swells. By decreasing the thickness of the resulting posts, the hydrogel can swell without losing robustness and/or delaminating (e.g., hydrogel post peeling away from the surface of the well).

The negative insert can further be prepared to vary the topography of the hydrogel post. For example, the negative insert can be prepared to have a patterned appearance at its surface, thereby providing a patterned hydrogel post. Nanometer-scale topography has been shown to be able to influence stem cell attachment, spreading, focal adhesion formation, cytoskeletal organization, differentiation, and microtissue formation. Further, this patterning allows for changing the surface roughness/evenness of the hydrogel post. This roughness may provide physical attachment points for cell attachment.

The height the hydrogel posts can be determined, for example, using a microscope to focus from the top of the hydrogel down to the substrate, using a microscope to focus from the substrate up to the top of the hydrogel, and by measuring the surface roughness of a hydrogel post as determined by atomic force microscopy.

In some embodiments, the negative insert can further constrain the diameter of the hydrogel posts by providing a physical barrier to the swelling of the hydrogel within the wells.

The negative insert used in the method can be any suitable material known to those skilled in the art. A particularly suitable negative insert can be, for example, polydimethylsiloxane (PDMS). PDMS is a hydrophobic, silicon-based organic polymer.

Other suitable negative inserts for use in the methods can be prepared using methods known in the art such as injection molding and 3D printing.

In some embodiments, the negative insert can further be prepared such to include wells within the negative insert. In this way, multiple hydrogel posts can be formed within a well of the multi-well plates.

The method further includes adding a hydrogel precursor solution to at least one well of the plurality of wells in the multi-well plate. In particular, the hydrogel precursor solution at least partially fills the wells of the multi-well plate. The hydrogel precursor solution can be, for example, a combination of a polymer and a multifunctional polymer crosslinker.

Suitable polymers for the hydrogel precursor solution are known by those skilled in the art and can include, for example, poly(ethylene glycol), hyaluronic acid, gelatin, collagen, MATRIGEL®, dithiol polymers (e.g., acrylamide), click-based composite hydrogels (as discussed in Polizzotti et al. Biomacromolecules 2008, 9:1084-1087, which is hereby incorporated by reference to the extent its disclosure is consistent with the present disclosure), poly(ethylene glycol)-diacrylate, poly(ethylene glycol)-vinyl sulfone, and the like. Particularly suitable polymers can be, for example, poly(ethylene glycol), thiolated hyaluronic acid, thiolated gelatin, collagen, and the like. Particularly suitable polymers can also be, for example, functionalized polymers. Functionalization of the polymer can be confirmed with $^1$H nuclear magnetic resonance spectroscopy, mass spectroscopy, Elman's reagent, UV-Vis spectroscopy, infrared spectroscopy, and other methods known to those skilled in the art, for example.

A particularly suitable functionalized polymer can be, for example, eight-arm poly(ethylene glycol) with terminal hydroxyl (—OH) groups (commercially available from JenKem Technology USA, Allen, Tex. and Laysan Bio, Inc., Arab, Ala.) that is functionalized with norbornene. Eight-arm poly(ethylene glycol) can be functionalized with norbornene as described in Fairbanks et al. (Adv. Mater. 2009, 21:5005-5010).

Other particularly suitable polymers are poly(ethylene glycols) that may be functionalized using click chemistry. "Click" chemistry is an extremely versatile method for chemically attaching biomolecules, which is used to describe the [3+2] cycloaddition between alkyne and azide functional groups. Azides and alkynes are largely inert towards biological molecules and aqueous environments, which allow the use of the Huisgen 1,3-dipolar cycloaddition to yield stable triazoles that are very difficult to oxidize or reduce. Both the copper(I)-catalyzed and copper-free strained-alkyne variant reactions are mild and very efficient. These reactions can also be performed in small volumes of aqueous solutions, are insensitive to oxygen and water, and robust to functional groups on peptides. Click chemistry allows for selectivity in conjugation reactions in biological samples such as, for example, oligonucleotides and proteins. Particularly suitable reagents for click chemistry are commercially available from Laysan Bio Inc. (Arab, Ala.).

Suitable multifunctional polymer crosslinkers for use in the hydrogel precursor solution are known by those skilled in the art. In particular, the multifunctional polymer crosslinker can be, for example, a bifunctional polymer crosslinker and a multifunctional polymer crosslinker (n>=2) and terminated with a functional group that can form a covalent bond with the polymer of the hydrogel precursor solution. Particularly suitable bi-functional polymer crosslinkers and multifunctional polymer crosslinkers can be, for example, polyethylene glycol dithiol (PEG-DT), protease-degradable crosslinkers and multi-arm poly(ethylene glycol) terminated with thiol (e.g., 4-arm PEG terminated with thiol). Alternative functional crosslinkers can be acrylate-functionalized crosslinkers such as, for example, PEG-diacrylate, PEG-dimethacrylate and the like (commercially available from Poly-Sciences, Inc., Warrington, Pa.). Suitable protease-degradable crosslinkers can be, for example, matrix metalloproteinase-degradable crosslinkers as described in Nagase and Fields (Biopolymers 1996, 40:399-416, which is hereby incorporated by reference to the extent it is consistent with the present disclosure). Alternatively, the polymer crosslinker can be, for example, a streptavidin-terminated polymer crosslinker and biotin-terminated polymer crosslinker. For polymers such as MATRIGEL®, for example, a crosslinker is not necessary.

The hydrogel precursor solution can further include an initiator. As known by those skilled in the art, hydrogel polymerization can occur in the absence of an initiator. An initiator can, however, induce polymerization and/or decrease the polymerization rate. Suitable initiators are known to those skilled in the art and can be, for example, chemical initiators and photoinitiators. Particularly suitable photoinitiators can be, for example, IRGACURE 2959 photoinitiator (commercially available from Ciba/BASF, Ludwigshafen, Germany), phosphinate initiators (e.g., lithium acylphosphinate salt and lithium phenyl-2,4,6-trimethylbenzoylphosphinate ("LAP")). Polymerization to form the hydrogel can also be performed by temperature change.

In another aspect, the hydrogel precursor solution can include a ligand as described herein. The density (concentration) of the ligand in an individual hydrogel post of a hydrogel array can be controlled by altering the concentration of the ligand in the hydrogel precursor solution.

In another aspect, a hydrogel array can be prepared to include hydrogel posts having a variable modulus. Hydrogel arrays can have a range of moduli. Hydrogel arrays having hydrogel posts with different moduli can be prepared by changing the concentration of the polymer, changing the amount of crosslinking, changing the stoichiometric ratio of the multifunctional polymer (e.g., thiol-polyethylene glycol-thiol (SH-PEG-SH)) to polymer ratio in the hydrogel precursor solution, changing the physical properties of the polymer backbone, changing the physical properties of the crosslinker and combinations thereof. The modulus can also be varied by changing the physical properties of the polymer backbone and/or the crosslinker. For example, 4-arm PEG of 20 kDa has a longer "arm" length than a 4-arm PEG of 10 kDa. Thus, using a 4-arm PEG of 10 kDa can produce a hydrogel of higher modulus than a 4-arm PEG of 20 kDa (see e.g., Toepke et al. 2013 Macromol. Mater. Eng. 298: 699-703, which is hereby incorporated by reference to the extent its disclosure is consistent with the present disclosure).

Suitable ratios can be from about 1:1 to about 4:1 (molar ratio). For example, the hydrogel modulus of a hydrogel using PEG-NB polymer and a dithiol crosslinker can be controlled, for example, by altering the ratio of PEG-NB to dithiol crosslinker by, for example, holding the PEG-NB wt % constant, then adding the crosslinker in a ratio that only crosslinks a portion of the PEG-NB arms such as, for example, about 25% to 100% crosslinking.

In another aspect, the hydrogel precursor solution can further include a cell. Suitable cells are known to those skilled in the art and can be, for example, embryonic stem cells (ESCs), ESC-derived neurons, ESC-derived Neural progenitor cells, ESC-derived astrocytes, ESC-derived microglial cells, ESC-derived endothelial cells, mesenchymal stem cells (MSCs), umbilical vein endothelial cells (UVECs), NIH 3T3 fibroblasts, dermal fibroblasts (DFs), fibrosarcoma cells (HT-1080s), and embryonic stem cells (ESCs), valvular interstitial cells, cardiomyocytes, neurons, pericytes, cancer cells such as, for example, melanoma cells, breast carcinoma cells and glioblastoma cells, hepatocytes, pancreatic beta cells and pancreatic islet cells.

In another aspect, the hydrogel precursor solution can further include a microsphere. Microspheres can contain molecules such as, for example, biomolecules, dyes and other molecules known to those skilled in the art. Microspheres can be degradable microspheres that dissolve or degrade to release the contents of the microsphere.

Following the addition of the hydrogel precursor solution to the wells of the multi-well plate, the method includes polymerizing at least a portion of the hydrogel precursor solution such that one or more polymerized hydrogel ("hydrogel post") attaches to the bottom surface of the wells of the multi-well plates. In one particularly suitable embodiment, the hydrogel precursor solution is polymerized by exposing the solution to ultraviolet light.

In some particularly suitable embodiments, the hydrogel precursor solution is selectively polymerized through the use of a photomask over the hydrogel precursor solution (see FIG. 1). Any photomask as known in the ultraviolet light arts can be used in the methods of the present disclosure. Typically, photomasks have been either one of two distinct varieties. One of these consists of a layer of a photographic emulsion on a transparent substrate which may be either a glass plate or a sheet of synthetic resin. The photographic emulsion is developed to produce the pattern of opaque and transparent areas desired.

The other type comprises a pattern of chromium deposited on a transparent glass substrate. The chromium may be deposited either by vacuum evaporation or by sputtering of a uniform film with subsequent etching to remove the unwanted portions. The pattern provides portions of "dark" regions that can block UV light and "light" regions that can allow UV light to pass through.

In one embodiment, a photomask that is ink printed on a plastic film. An exemplary printed pattern may include 3000 dots per square inch and 200 lines per square inch.

Other suitable methods of polymerization, including temperature and chemical polymerization, can be used to selectively polymerize the hydrogel precursor solution.

After polymerization, the unpolymerized hydrogel precursor solution is removed from the wells of the multi-well plates. The unpolymerized solution can be removed using any means known in the art. As shown in FIG. 1, the unpolymerized solution is removed with a pipette.

In some embodiments, when a negative insert has been used, the method further includes separating the negative insert from the hydrogel posts. In one suitable embodiment, the negative insert is removed by altering the temperature of the hydrogel causing the hydrogel to swell, forcibly removing the negative inset. Upon separation of the negative insert from the hydrogel posts, the polymerized hydrogel posts remain attached to the bottom surface of the wells of the multi-well plate to result in the hydrogel array.

Hydrogel Arrays

In another aspect, the present disclosure is directed to a hydrogel array including hydrogel posts having variable modulus, variable shear modulus, variable ligand identity, variable ligand density and combinations thereof. The hydrogel arrays including hydrogel posts having variable modulus, variable shear modulus, variable ligand identity, variable ligand density and combinations thereof can be prepared according to the methods described herein above.

The hydrogel array may include hydrogel posts having a variable ligand density (or concentration) of an individual hydrogel post of the hydrogel array can range up to 7.7 pmol/mm$^2$ for a planar surface. For example, the ligand density can be from 0 pmol/mm$^2$ to about 7.7 pmol/mm$^2$. Suitable ligand density can also be from about 0.25 mM to about 4 mM. Suitable ligands are described herein. The ligand is immobilized to the hydrogel post as described herein.

The hydrogel array may further include hydrogel posts having a variable ligand identity. For example, at least two different ligands can be incorporated into an individual hydrogel post. The ligand is immobilized to the hydrogel post as described herein. Suitable ligands are known to those skilled in the art and can be, for example, any biomolecule containing a cysteine and/or functionalized with a thiol. Thiol-functionalizing of ligands can be performed using commercially available kits (e.g., Traut's Reagent (2-iminothiolane.HCl), Thermo Fischer Scientific, Rockford, Ill.). Suitable ligands can be, for example, proteins, peptides, nucleic acids, polysaccharides, lipids, biomimetic materials and other molecules, and combinations thereof. Particularly suitable proteins can be, for example, adhesion proteins. Particularly suitable adhesion proteins can be, for example, fibronectin, selectin, integrin, cadherin and combinations thereof. Particularly suitable peptides can be, for example, adhesion peptides. As used herein, an "adhesion peptide" refers to an amino acid sequence obtained from an adhesion protein to which cells bind via a receptor-ligand interaction. Examples of particularly suitable peptide sequences are provided in Table 1, below.

TABLE 1

Peptides sequences for hydrogel arrays.

| Name/Source | Sequence | SEQ ID NO |
|---|---|---|
| Fibronectin | RGD | n/a |
| Fibronectin | RGDS | 1 |
| Fibronectin | CRGDS | 2 |
| Fibronectin | GRGDSP | 3 |
| Fibronectin (referred to as "RGD-PHSRN") | CRGD-(G)$_{13}$-PHSRN | 4 |
| Fibronectin | CRGD-(SG)$_5$-PHSRN | 5 |
| Acetylated-CRGDSP | Ac-CRGDSP | 6 |
| Acetylated-GCYGRGDSPG | Ac-GCYGRGDSPG | 7 |
| "Cyclic RGD" | cyclic (RGD{d-Phe}C | 8 |
| non-bioactive scrambled peptide | RDGS | 9 |
| non-bioactive scrambled peptide | CRDGS | 10 |
| Fibronectin | GCYGRGDSPG | 11 |
| Fibronectin | PHSRN | 12 |
| Fibronectin | GWGGRGDSP | 13 |
| Fibronectin | SIDQVEPYSSTAQ | 14 |
| Laminin | GRNIAEIIKDI | 15 |

TABLE 1-continued

Peptides sequences for hydrogel arrays.

| Name/Source | Sequence | SEQ ID NO |
|---|---|---|
| Laminin | DITYVRLKF | 16 |
| Laminin | DITVTLNRL | 17 |
| Laminin | GRYVVLPR | 18 |
| Laminin | GNRWHSIYITRFG | 19 |
| Laminin | GASIKVAVSADR | 20 |
| Laminin | GTTVKYIFR | 21 |
| Laminin | GSIKIRGTYS | 22 |
| Laminin | GSINNNR | 23 |
| Laminin | SDPGYIGSR | 24 |
| Laminin | YIGSR | 25 |
| Collagen I | GTPGPQGIAGQGVV | 26 |
| Collagen I | GTPGPQGIAGQRVV | 27 |
| Collagen II | MNYYSNS | 28 |
| Vitronectin | KKQRFRHRNRKG | 29 |
| Vascular Endothelial Growth Factor-Receptor Binding Peptide | GGGKLTWQELYQLKYKGI | 30 |
| Vascular endothelial growth factor receptor binding peptide (VR-BP) | KLTWQELYQLKYKGI | 31 |
| Bone morphogenetic protein-2 (BMP-2) receptor binding peptide | KIPKASSVPTEL | 32 |
| Bone morphogenic protein receptor-binding peptide | KIPKASSVPTELSAISTLYL | 33 |
| Heparin proteoglycan-binding peptide (HPG-BP) | KRTGQYKL | 34 |
| MMP-degradable crosslinking peptide | KCGGPQGIWGQGCK | 35 |
| MMP-degradable crosslinking peptide | KCGGPQGIAGQGCK | 36 |

In another aspect, ligands can be ligands that are suspected of binding or interacting with a cell to affect cell attachment, spreading, migration, proliferation, and differentiation. This aspect allows for using the hydrogel arrays to specifically screen ligands for effects on the cells such as, for example, cell attachment, spreading, migration, proliferation, and differentiation. Additionally, ligands of unknown function can be immobilized in combination with a cell attachment ligand to screen for changes in cell attachment, spreading, migration, proliferation, and differentiation.

The hydrogel array may further include hydrogel posts having variable moduli. Hydrogel arrays can have a range of stiffness (expressed herein as elastic modulus). For example, hydrogels with different moduli can be prepared by changing the concentration of the polymer and/or changing the stoichiometric ratio of the multifunctional polymer (e.g., the bifunctional polymer thiol-polyethylene glycol-thiol (SH-PEG-SH)) to polymer ratio in the hydrogel precursor solution. Suitable ratios can be from about 1:1 to about 4:1 (molar ratio). Particularly suitable elastic moduli of the hydrogel array can be similar to the elastic modulus of a given tissue type. For example, the hydrogel array can have an elastic modulus similar to brain tissue, which is less than 1 kPa. The hydrogel array can have an elastic modulus similar to healthy breast tissue (as opposed to diseased breast tissue), which is about 1 kPa. The hydrogel array can have an elastic modulus similar to fat tissue, which is about 3 kPa. The hydrogel array can have an elastic modulus similar to muscle tissue, which is about 10 kPa. The hydrogel array can have an elastic modulus similar to healthy lung tissue (as opposed to diseased lung tissue), which is from about 5 kPa to about 30 kPa. The hydrogel array can have an elastic modulus similar to skin, which is from about 30 kPa to about 50 kPa. The hydrogel array can have an elastic modulus similar to fibrotic tissue, which is from about 20 kPa to about 60 kPa.

Hydrogel modulus as well as determining other mechanical features of the hydrogel can be performed using methods known by those skilled in the art. Dynamic mechanical analysis of hydrogels can be performed using an Ares-LS2 rheometer (commercially available from TA Instruments, New Castle, Del.) to evaluate the modulus of the hydrogels. For example, hydrogel samples can be crosslinked in 8.0 mm diameter 1.2 mm depth Teflon wells for 3 seconds using 365 nm UV light at a dose rate of 90 mW cm$^{-2}$. After swelling the samples to equilibrium in phosphate buffered saline and cutting to a final diameter of 8.0 mm, the samples can be loaded onto 8 mm diameter cross-heads and loaded with 0.2 Newtons of normal force. If the samples are not sufficiently robust to withstand 0.2 Newtons of normal force, the cross-heads can be set at a 1.0 mm gap distance. Samples are then sheared by the cross-heads in an oscillatory manner at a constant frequency of 10 Hz. Shear strains can range from about 0.1% to about 20%. Shear stress, shear strain and the elastic moduli can be calculated as follows:

$$\sigma = Tr/\pi r^2/2 \quad \text{(Eq. 1)}$$

Eq. 1: Sample shear stress based on torque (T), sample radius (r) and the sample polar moment of inertia ($\pi r^2/2$).

$$\epsilon = \Delta\theta tr/L \quad \text{(Eq. 2)}$$

Eq. 2: Sample shear strain based on rotation rate ($\Delta\theta$), time (t), sample radius (r) and sample height (L).

$$G' = \sigma/\epsilon \cos\delta \quad \text{(Eq. 3)}$$

Eq. 3: Storage modulus (G') of the sample can be calculated by taking the sample stress ($\sigma$) divided by the sample strain ($\epsilon$) and multiplying by the cosine of the phase angle ($\delta$). A strain average value can be computed by testing using multiple strains.

Hydrogel arrays can also be prepared to have individual hydrogel posts having any desired sizes (e.g., by varying negative insert size, shape, and topography). Suitable individual hydrogel post size of the hydrogel array can be small enough to accommodate a single cell, but also large enough to accommodate many cells, for example. Thus, the individual hydrogel post size of the hydrogel array can have any desired diameter (as discussed above, the diameter of the hydrogel post will be constrained by the size of the well in the multi-well plate).

Hydrogel arrays can also be prepared to have individual hydrogel posts having any desired height. The height of the hydrogel posts can be determined by the thickness of the negative insert assembled with the multi-well plate while performing the method. Thus, the hydrogel posts of the hydrogel array can have any desirable height. Suitable heights of the hydrogel posts can be from 20 micrometers (μm) to about 1 millimeter, however, hydrogel posts can be made much higher than 1 millimeter if desired.

In another aspect, the hydrogel array can include the hydrogel posts and further include at least one layer of hydrogel on the top surface of the posts. Particularly, once the hydrogel posts are prepared, additional hydrogel precursor solution can be added to the top surface of the posts and polymerized as described above to result in additional layer(s) of polymerized hydrogel. Various ligands, cells, microspheres, and the like can be included and/or attached to each layer of additional hydrogel.

Methods of Screening Molecule-Molecule Interactions Using the Patterned Hydrogel Arrays In yet another aspect, the present disclosure is directed to a method for screening for molecule-molecule interactions. The method includes preparing a hydrogel array, wherein the hydrogel array includes at least one hydrogel post in a well of the hydrogel array; contacting the at least one hydrogel post with a molecule known to or suspected of interacting with at least one ligand; and analyzing the hydrogel array.

The hydrogel post(s) can be prepared as described herein by adding a hydrogel precursor solution including at least one ligand to at least one well of a multi-well plate; polymerizing the hydrogel precursor solution; and removing any unpolymerized hydrogel precursor solution, thereby forming at least one hydrogel post including the at least one ligand that is covalently attached to the bottom surface of the well.

The method further includes contacting the hydrogel posts of the hydrogel array with a molecule known to or suspected of interacting with the at least one ligand by including the molecule in a binding solution. As used herein, a "binding solution" refers to a solution developed to allow for investigating the potential interaction between molecules. The binding solution can be further modified to include components designed to strengthen or weaken molecule interactions such as, for example, ionic components, pH components and the like.

The hydrogel array can be analyzed using methods known to those skilled in the art. For example, hydrogel arrays can be analyzed using fluorescence, microscopy, and the like.

Methods of Screening a Cell-Surface Interaction Using the Hydrogel Arrays

In another aspect, the present disclosure is directed to a method of screening a cell-surface interaction using the hydrogel arrays as prepared herein to include hydrogel posts having variable densities (moduli), variable ligand identities, variable ligand densities, and combinations thereof. The ligand to be screened using the hydrogel array of the present disclosure can be a ligand that is known or suspected of binding or interacting with a cell.

The method further includes contacting a cell with a hydrogel array. As used herein, "contacting a cell" refers to seeding cells onto the hydrogel array for the purpose of analyzing the cells and the hydrogel array. As known by those skilled in the art a cell suspension is typically transferred to a substrate and cells are given sufficient time to adhere to the substrate.

In another embodiment, cells can be incorporated in to the hydrogel of the hydrogel array using a hydrogel precursor solution that includes a polymer, a crosslinker and a cell.

The cells are then cultured for a desired time such as, for example, about one hour to about 30 days. After the desired time, cells can be analyzed by microscopy such as, for example, immunofluorescence microscopy, phase contrast microscopy, light microscopy, electron microscopy and combinations thereof. Cells can be analyzed for cell attachment, cell spreading, cell morphology, cell proliferation, cell migration, cell differentiation, protein expression, and combinations thereof.

Suitable cells can be any cell known by those skilled in the art. Particularly suitable cells can be, for example, embryonic stem cells (ESCs), ESC-derived neurons, ESC-derived Neural progenitor cells, ESC-derived astrocytes, ESC-derived microglial cells, ESC-derived endothelial cells, mesenchymal stem cells (MSCs), umbilical vein endothelial cells (UVECs), NIH 3T3 fibroblasts, dermal fibroblasts (DFs), fibrosarcoma cells (HT-1080s), and embryonic stem cells (ESCs), valvular interstitial cells, cardiomyocytes, neurons, pericytes, cancer cells such as, for example, melanoma cells, breast carcinoma cells and glioblastoma cells, hepatocytes, pancreatic beta cells and pancreatic islet cells.

The method may further include contacting the cell with a soluble molecule by including the soluble molecule in the culture medium in which the cells on the hydrogel post of the hydrogel array are cultured. Particularly suitable soluble molecules may be growth factors and proteoglycans. Suitable growth factors may be, for example, proteins from the transforming growth factor beta superfamily, fibroblast growth factor family of growth factors, platelet derived growth factor family of growth factors and combinations thereof. Particularly suitable growth factors may be, for example, vascular endothelial growth factor, bone morphogenetic proteins, fibroblast growth factor, insulin-like growth factor and combinations thereof. Suitable proteoglycans may be, for example, proteoglycans with heparin, heparan sulfate, or chondroitin glycosaminoglycan side chains.

The methods and hydrogel arrays of the present disclosure allow for exceptional control over the density of the ligand on the hydrogel post as well as exceptional control over the identity of the ligand on the hydrogel post. The stiffness of the hydrogel post of the hydrogel array can also be controlled. This control allows for screening for specific parameters of substrates for the culture of cells, which may alter and influence the outcome of the cellular response to the substrate and culture environment. The hydrogel arrays of the present disclosure further allow for screening combinations of ligands. Thus, the hydrogel arrays of the present disclosure present a tool to perform high-throughput multi-variable biological screens on a single surface for identifying specific parameters of substrates that may alter and influence the outcome of the cellular response to the substrate and culture environment.

The disclosure will be more fully understood upon consideration of the following non-limiting Examples.

EXAMPLES

Materials and Methods

PEG-Norborne Synthesis

Eight-arm poly(ethylene glycol) (PEG) with terminal hydroxyl groups (—OH) and a molecular weight of 20 kDa was purchased from JenKem Technology USA (Allen, Tex.). Anhydrous pyridine, 4-dimethylamino)pyridine (DMAP), 5-norbornene-2-carboxylic acid, diethyl ether, and deuterated chloroform ($CDCl_3$, 99.8%) with 0.03% v/v tetramethylsilane (TMS) were purchased from Sigma Aldrich (St. Louis, Mo.). N,N'-Dicyclohexylcarbodiimide (DCC) and anhydrous dichloromethane (DCM) were purchased from ACROS Organics (Geel, Belgium). SNAKESKIN dialysis tubing having a 3.5K molecular weight cut-off was purchased from Thermo Fisher Scientific (Waltham, Mass.).

Eight-arm PEG-OH was functionalized with norbornene to utilize the thiol-ene chemistry for photopolymerization and immobilization of bioactive ligands as described in Fairbanks et al. Adv. Mater. 2009, 21:5005-5010; Impellitteri et al. Biomaterials 2012, 33:3475-84; Belair and Murphy Acta Biomater. 2013; and Gould et al. Acta Biomater 2012, 8:3201-3209. The PEG-norbornene (PEG-NB) product of the functionalization reaction was filtered through a medium fritted Buchner funnel to remove salts formed during the reaction. The filtrate was then precipitated in 900 mL cold diethyl ether and 100 mL hexane. The solids were collected on qualitative grade filter paper and air dried overnight. The PEG-NB product was purified by dialysis against 4 L of $dH_2O$ at 4° C. for 72 hours (with water change every 8 hours) using rehydrated SNAKESKIN dialysis tubing to remove residual norbornene acid and subsequently freeze dried.

Norbornene functionalization of >90% was confirmed with 1H nuclear magnetic resonance spectroscopy. Samples were prepared at 6 mg/mL in $CDCl_3$ with TMS internal standard. Free induction decay (FID) spectra were obtained using spectroscopy services provided by the National Magnetic Resonance Facility at Madison on a Bruker Instruments Avance III 500i spectrometer at 400 MHz and 27° C.

Hydrogel Array Formation

Hydrogel arrays used for these experiments were composed of hydrogel posts formed in individual wells of glass bottom multi-well plates and immobilized to the bottom of each well. The hydrogels were formed by photopolymerization whereby a photomas (attached to the outer surface of the bottom of the plate) was used to define the shape and a negative insert (inserted into the wells through the open face of the plate) was used to define the height and surface topography of the hydrogels in each well. The method of preparing a hydrogel array in a multi-well plate is further described below.

Glass Bottom Plate Silanization

Sterile glass bottom 96-well plates were purchased from In Vitro Scientific (Sunnyvale, Calif.). Ethanol, 3-mercaptopropyl trimethoxysilane (3-MPTS), and dithiothreitol (DTT) were purchased from Sigma Aldrich (St. Louis, Mo.).

Glass bottom 96-well plates were silanized with 3-MPTS to create substrates presenting thiol groups capable of participating in thiol-ene reaction with PEG-NB and subsequently enable covalent immobilization of PEG-NB hydrogels (Seo et al. Colloids Surf B Biointerfaces 2012, 98:1-6). Liquid-phase silanization was performed with slight modification from procedures previously described (Seo et al. Colloids Surf B Biointerfaces 2012, 98:1-6; Halliwell et al. Anal Chem 2001, 73:2476-2483; and Cras et al. Biosens Bioelectron 1999, 14:683-688). Each well of the glass bottom 96-well plate was filled with 50 µL of 2.5% v/v 3-MPTS in 95% ethanol and allowed to incubate for 4 hours, at room temperature and covered from light. Excess silanes were removed from the surface of the coverslips by rinsing with 70% ethanol and dried with vacuum. Prior to use, silanized glass bottom plates were treated with 10 mM DTT in PBS for 30 minutes at 37° C. to reduce disulfides formed on the surface and to increase free thiols available at the surface (Vistas et al. Appl Surf Sci 2013, 286:314-318).

Fabrication of Photomasks

The layout and geometries for the photomasks were drawn using Adobe Illustrator and printed onto transparency films using a high resolution commercial laser printing service provided by ImageSetter (Madison, Wis.).

Fabrication of Negative Inserts

The layout and geometries for the negative were drawn using Solidworks and made by fused deposition of Accura 60 plastic using a Dimension Elite printer through services provided by the Rapid Prototyping Consortium in the Wisconsin Institutes for Discovery.

Hydrogel Post Polymerization and Immobilization

PEG-NB was functionalized as described above. Bi-functional PEG dithiol (PEG-DT) crosslinker (3.4 kDa) was purchased from Laysan Bio (Arab, Ala.). Irgacure 2959 photoinitiator was purchased from Ciba/BASF (Ludwigshafen, Germany). Cysteine-terminated peptides were purchased from GenScript USA (Piscataway, N.J.). Omnicure Series 1000 UV post cure lamp (365 nm wavelength), light guide, and collimating adapter were purchased from Lumen Dynamics Group (Ontario, Canada). Silanized glass plates, photomasks, and negative inserts were prepared as described above.

Hydrogel precursor solutions were prepared by combining PEG-NB, PEG-DT, peptides, and photoinitiator and diluted to desired concentrations with phosphate buffered saline (PBS) immediately prior to hydrogel posts formation.

Hydrogel precursor solutions were deposited into the bottom of each well in the 96-well plate (35 µL per well) (FIG. 3A). The negative insert was applied to the top face of the 96-well plate such that the protrusions on the negative insert were inserted into each well (see FIGS. 3B & 3C). The protrusions of the negative insert were designed with height dimensions that would allow the protrusions to directly contact the hydrogel precursor solution contained within each well. The photomask was applied to the outer surface of the bottom of the 96-well plate so that transparent patterns were directly aligned with each of the hydrogel precursor-containing wells. Hydrogel precursor solutions were polymerized by UV-initiated photo-crosslinking for 20 seconds at 5 mW/cm$^2$, with the light penetrating through the transparent patterns on the photomask and the bottom of the glass bottom 96-well plate (see FIG. 3D). The negative insert was removed from the 96-well plate. The un-polymerized hydrogel precursor solutions in each well were removed. The resulting polymerized hydrogel posts were covalently attached and immobilized onto the silanized glass bottom of each well in the 96-well plate (see FIG. 4A). Recall that the silanization procedure produced glass bottom wells that were functionalized with thiol-terminated silanes that were capable of participating in the thiol-ene reaction used for hydrogel precursor solution polymerization, which effectively crosslinked the hydrogel network to the surface-bound silanes. The resulting glass-immobilized hydrogel spots in each well of the 96-well plate was sterilized for 1 hour in 70% ethanol and washed with PBS to remove any remaining unreacted components.

The above methods were used to prepare arrays in 12-well plates as well (see FIGS. 4B & 4C). As further shown in FIG. 4C, the hydrogel arrays can be further patterned such that the hydrogel post within a well has a well itself.

The bioactivity of each hydrogel spot in the array was defined by both the identity and concentration of the peptides incorporated therein as previously demonstrated by Nguyen et al. Biomaterials 2014, 35:2149-2161; Hansen et al. Biomaterials Science 2014, 5:745-756; Musah et al. PNAS 2014, 111:13805-13810). Peptides used in these Examples were CRGDS (SEQ ID NO:2), and a non-bioactive scrambled peptide CRDGS (SEQ ID NO:10). To modulate the bioactivity of each hydrogel spot, different peptides were added to the hydrogel precursor solutions and, following UV-initiated crosslinking, the resulting polymerized hydrogel networks each presented different immobilized peptides. For all arrays, a total of 4 mM of peptides were incorporated into the hydrogel network. To concurrently change the bioactivity of the hydrogel spots via control of peptide identity and concentration, the desired concentration of the chosen bioactive peptide (containing the "RGD" sequence) was determined and the non-bioactive scrambled peptide CRDGS (SEQ ID NO:10) was supplemented to maintain a total peptide concentration of 4 mM in the hydrogel precursor solution.

The modulus of each hydrogel spot in the hydrogel array was defined by the total concentration of PEG in the crosslinked hydrogel network. Increasing the concentration of PEG-NB in the hydrogel precursor solution resulted in a larger amount of PEG crosslinked into the polymerized network, which resulted in an increase in the compressive modulus as previously demonstrated by Toepke et al. Macromolecular Materials and Engineering 2013, 298: 699-703).

Example 1

In this Example, a hydrogel array could be used to determine the effects of substrate properties on initial stem cell adhesion.

Poly (ethylene glycol) (PEG) hydrogel arrays are formed in glass bottom 96-well plates as described above (see, FIGS. 3A-3D). UV-initiated thiol-ene crosslinking simultaneously polymerizes the hydrogel and immobilizes the hydrogel spots in each well of the plate to result in the hydrogel array.

Hydrogel solutions with fibronectin-derived peptides, fluorescent microspheres and a dithiol crosslinker are deposited onto the SAMs and sandwiched with a silanized glass slide. Individual hydrogel spots of the hydrogel array could be prepared to include varying amounts of fluorescently-tagged peptides as well as varying amounts of fluorescent microspheres. Hydrogel solutions with varying PEG or crosslinker concentration are also prepared prior to crosslinking to change the stiffness, peptide identity or peptide concentration Human mesenchymal stem cells (hMSCs) are cultured on posts with varying PEG concentrations (4 wt. %, 6 wt. % and 8 wt. %) to change stiffness and are monitored for changes in initial cell adhesion and spreading. Human embryonic stem cells (hESCs) are cultured on PEG-NB hydrogel arrays prepared using 8 wt. % PEG and 75% crosslinking with PEG-dithiol and functionalized with 2 mM of varying fibronectin-derived integrin-binding peptides (blank, non-bioactive scrambled peptide RDGS (SEQ ID NO:9), RGDS (SEQ ID NO:2), RGD-PHSRN (SEQ ID NO:4); Ac-GCYGRGDSPG (SEQ ID NO:7); and cyclic RGD (SEQ ID NO:8)) and are monitored for changes in initial cell adhesion and spreading.

Additionally, hMSCs are seeded on 8-arm PEG-NB (20 kDa) hydrogel arrays (8 wt. % PEG and 25% crosslinking with PEG-dithiol, 3.4 kDa) and functionalized without peptide, with 1 mM RGD, with 2 mM RGD and 4 mM RGD. Cells are allowed to adhere for 24 hours and images may be obtained using phase contrast microscopy.

Example 2

In this Example, a patterned hydrogel array could be used to investigate endothelial cell tubule network formation (termed "tubulogenesis") in vitro.

Specifically, patterned hydrogel arrays are composed of 8-arm, 20 kDa polyethylene glycol) functionalized with norbenene. The patterned hydrogel arrays include hydrogel spots contained from 30 mg/mL to 60 mg/mL PEG, from 30-70% crosslinking with an MMP-degradable crosslinking peptide (KCGGPQGIWGQGCK, SEQ ID NO:35 or KCGGPQGIAGQGCK, SEQ ID NO:36) and 0.25 mM to 2 mM of a cell adhesive peptide (CRGDS, SEQ ID NO:2). Patterned hydrogel array spots are seeded with human umbilical vein endothelial cells (HUVECs), human induced pluripotent stem cell-derived endothelial cells (iPSC-ECs), and human embryonic stem cell-derived endothelial cells (hESC-ECs) in culture media containing standard growth medium for each cell type (Medium 199 and EGM-2 BUL-LETKIT™ (Lonza, Basel, Switzerland) for HUVECs, VAS-CULIFE® and VEGF LifeFactors for iPSC-ECs and hESC-ECs (Lifeline Cell Technology, Frederick, Md.)).

What is claimed is:

1. A method of preparing a hydrogel array comprising a multi-well plate, the multi-well plate comprising a plurality of wells wherein the plurality of wells independently comprises a hydrogel post, the method comprising
thiol-functionalizing a bottom surface of the plurality of wells;
adding a hydrogel precursor solution to at least one well of the plurality of wells;
selectively polymerizing a portion of the hydrogel precursor solution in the at least one well;
removing unpolymerized hydrogel precursor solution from the plurality of wells, wherein the polymerized hydrogel forms a hydrogel post covalently immobilized within the at least one well and wherein the hydrogel post is surrounded by a hydrogel-free background; and
forming an additional hydrogel layer on the hydrogel post.

2. The method of claim 1 wherein the thiol-functionalizing of the bottom surface of the plurality of the wells is by silanization.

3. The method of claim 1 further comprising assembling the multi-well plate with a negative insert, wherein the negative insert fills a portion of a volume of the well.

4. The method of claim 1 wherein the multi-well plate is selected from the group consisting of a glass-bottom multi-well plate and a polystyrene multi-well plate.

5. The method of claim 4, wherein the multi-well plate is selected from the group consisting of 4-well plates, 6-well plates, 8-well plates, 12-well plates, 24-well plates, 32-well plates, 96-well plates, and 384-well plates.

6. The method of claim 1 wherein the hydrogel precursor solution is polymerized by exposure to ultraviolet light.

7. The method of claim 1 wherein the hydrogel precursor solution comprises a ligand.

8. The method of claim 7 wherein the ligand is selected from consisting of a protein, a peptide, a nucleic acid, a polysaccharide, a lipid, and combinations thereof.

9. The method of claim 1 wherein the at least one hydrogel post comprises a variable modulus, a variable ligand identity, a variable ligand density and combinations thereof.

10. A method of preparing a hydrogel array comprising a multi-well plate, the multi-well plate comprising a plurality of wells wherein at least one well independently comprises multiple hydrogel posts, the method comprising:
thiol-functionalizing a bottom surface of the plurality of wells;
adding a hydrogel precursor solution to at least one well of the plurality of wells;
assembling the multi-well plate with a negative insert for each of the at least one well, wherein the negative insert comprises wells configured to allow multiple hydrogel posts to be formed in the well assembled with the negative insert;
selectively polymerizing a portion of the hydrogel precursor solution in the at least one well; and
removing unpolymerized hydrogel precursor solution from the plurality of wells, wherein the polymerized hydrogel forms multiple hydrogel posts covalently immobilized within each of the at least one well.

* * * * *